United States Patent [19]

Goulet

[11] Patent Number: 5,500,207

[45] Date of Patent: Mar. 19, 1996

[54] METHOD OF WHITENING TEETH AND COMPOSITION THEREFORE

[76] Inventor: Marie-Kateri Goulet, 3605 The Boulevard, Montreal, Quebec, Canada, H3Y 1S6

[21] Appl. No.: 344,589

[22] Filed: Nov. 18, 1994

[51] Int. Cl.⁶ ............................................. A61K 7/22
[52] U.S. Cl. ............................................. 424/54
[58] Field of Search ................................ 424/54

[56] References Cited

U.S. PATENT DOCUMENTS

| | | |
|---|---|---|
| 3,577,521 | 5/1971 | Scheller et al. |
| 4,592,487 | 6/1986 | Simon et al. |
| 4,988,500 | 1/1991 | Hunter et al. |
| 5,234,342 | 8/1993 | Fischer |
| 5,310,563 | 5/1994 | Curtis et al. ............ 424/616 |

FOREIGN PATENT DOCUMENTS 2066917  10/1992  Canada.

*Primary Examiner*—Paul J. Killos

[57] ABSTRACT

A chewing gum or wax base is mixed with a tooth whitening agent such as carbamide peroxide and is conditioned into pieces of chewing gum or wax. Mastication of these on a regular basis helps in whitening teeth in a person in need of a tooth whitening treatment.

6 Claims, No Drawings

METHOD OF WHITENING TEETH AND COMPOSITION THEREFORE

BACKGROUND OF INVENTION

1. Field of the Invention

This invention relates to a method of whitening teeth and a composition therefor. More particularly the present invention relates to a composition including a chewing gum or wax base and a tooth whitening agent preferably conditioned as a piece of chewing gum or wax and which as a result of mastication provides a particularly interesting method of whitening teeth.

2. Description of Prior Art

Tooth whitening is a treatment which is in great demand as it is aesthetically important to have teeth as white as possible. One way of doing it is by means of a treatment at the dentist who treats the teeth of a patient with a bleaching agent. Normally, hydrogen peroxide is used as it is very effective. Other bleaching agents are also used as is well known to those skilled in the art. An example of such agents includes carbamide peroxide. This ingredient is sometimes conditioned in a paste for direct application to the teeth or in a tooth paste. However, since tooth whitening requires substantial contact of the teeth with the active ingredient, it was found that the occasional applications of a whitening agent by the dentist or by the patient himself, and even the occasional use of a tooth whitening tooth paste are not sufficient to provide a noted improvement.

For further background, reference is made to the following:

Canadian Patent: 2,066,917 Oct. 24, 1992

U.S. Pat. Nos.: 5,234,342 Aug. 10, 1993 4,988,500 Jan. 29, 1991 4,592,487 Jun. 3, 1986 3,577,521 May 4, 1971

SUMMARY OF INVENTION

It is therefore an object of the present invention to provide a method which ensures an easy and repeated contact of the teeth of a person with a tooth whitening agent.

It is another object of the present invention to provide a composition including a tooth whitening agent which is conditioned in a piece of chewing gum or wax.

The above and other objects of the invention may be achieved by providing a composition for whitening teeth which comprises a chewing gum or wax base and a tooth whitening agent.

The preferred whitening agent is carbamide peroxide although any other stable conventional whitening agent may be used.

A preferred composition according to the invention is conditioned as a piece of chewing gum or wax including, for example, about 10% by weight of a whitening agent which is for example carbamide peroxide.

DESCRIPTION OF PREFERRED EMBODIMENTS

EXAMPLE

A chewing gum base was mixed with 10% by weight of carbamide peroxide, and the mixture was conditioned into a plurality of pieces of chewing gum. A person in need of tooth whitening was given a two week supply of the thus obtained pieces of chewing gum, with instruction to chew four or five pieces a day for two weeks.

An appreciable whitening of the teeth was noted.

It is understood that the invention is not limited to the example given above, except as defined by the appended claims.

I claim:

1. Composition for whitening teeth which comprises a chewing gum or wax base and a tooth whitening agent comprising carbamide peroxide.

2. Composition according to claim 1, which comprises about 10% by weight of carbamide peroxide.

3. Composition according to claim 1, conditioned as a piece of chewing gum or wax.

4. A method of whitening teeth which comprises masticating a composition according to claim 1.

5. A method of whitening teeth which comprises masticating a composition according to claim 2.

6. A method of whitening teeth which comprises masticating a composition according to claim 3.

* * * * *